US005792171A

United States Patent [19]

Burdenko et al.

[11] Patent Number: 5,792,171

[45] Date of Patent: Aug. 11, 1998

[54] ACUPUNTURE METHOD AND DEVICE

[76] Inventors: Igor Burdenko, 34 Joyce Rd., Wayland, Mass. 01778; Stas Gavronsky, 209 Bishop Dr., Framingham, Mass. 01701

[21] Appl. No.: 838,274

[22] Filed: Apr. 17, 1997

[51] Int. Cl.[6] .................... A61B 17/34

[52] U.S. Cl. .................... 606/189; 601/166

[58] Field of Search .................... 606/185, 186, 606/188, 189

[56] References Cited

U.S. PATENT DOCUMENTS

| | | | |
|---|---|---|---|
| 3,905,375 | 9/1975 | Toyama | 606/189 |
| 4,479,496 | 10/1984 | Hsu | 606/189 |
| 4,950,279 | 8/1990 | Chang | 606/189 |
| 5,624,460 | 4/1997 | Yoo | 606/189 |

FOREIGN PATENT DOCUMENTS

| | | | |
|---|---|---|---|
| 2589727 | 5/1987 | France | 606/189 |

*Primary Examiner*—Michael Buiz

*Assistant Examiner*—David O. Reip

[57] ABSTRACT

A method of underwater acupuncture which advantageously uses a synergistic effect resulting from a combined use of acupuncture and a water therapy treatment. A device for carrying out the method comprises an enclosure (11) which is sealed at one end and has a flange (33) on the opposite open end. The sealed end has a resilient tip (22) and supports a sterile acupuncture needle (26) inside the enclosure. The flange has an adhesive outer tape (32) for sealingly attaching the device to the skin of a patient in the area of an acupuncture point. The acupuncture needle (26) is guided through a longitudinal channel (14) of a guide tube (24) inserted into the enclosure (11) and can be brought into contact with the skin of the patient by pushing on the aforementioned resilient tip (22).

33 Claims, 1 Drawing Sheet

ACUPUNTURE METHOD AND DEVICE

FIELD OF THE INVENTION

The present invention relates to medical treatment, and more particularly to an acupuncture method and device.

BACKGROUND OF THE INVENTION

Acupuncture is a method of encouraging the body to promote natural healing and to improve functioning. This is done by inserting needles and applying heat or electrical stimulation at very precise acupuncture points.

The classical Chinese explanation is that channels of energy run in regular patterns through the body and over its surface. These channels, called meridians, are like rivers flowing through the body to irrigate and nourish the tissues. Blood flow and nervous pulses also follow meridians to run through the body to various parts, structures and organs. An obstruction in the movement of these energy rivers is like a dam that backs up the flow in one part of the body and restricts it in others. Any obstruction and blockages or deficiencies of energy, blood and nervous pulses would eventually lead to disease.

The meridians can be influenced by needling the acupuncture points: the acupuncture needles unlock the obstruction at the dams, and reestablish the regular flow through the meridians. Acupuncture treatment can, therefore, help the body's internal organs to correct imbalances in their digestion, absorption, and energy production activities, and in circulation of their energy through the meridians.

Modern science explains the functions of acupuncture in two major ways:

1. Needling the acupuncture points stimulates the nervous system to release chemicals in the muscles, spinal cord, and brain. These chemicals will either change the sensation of pain, or they will trigger the release of other chemicals and hormones which influence the body's own internal regulating system.
2. Modern science reveals that the very basic unit of the body is cell. Cells' movement follow the movement of electrons. The electrons inside the cell act according to their own regular patterns. We call all these electrons in a living body bioelectrons.

Energy flow in the meridians is the direct or indirect transportation of bioelectrons. Meridians are the pathways where bioelectrons move more frequently than in other parts of the body. When positive and negative charges in the bioelectronic movements are not balanced, the cells would act abnormally.

All the external factors, such as mechanical, physical, chemical, biological and internal factors such as mental, hereditary, constitutional can cause and force the body's bioelectrical movement turn to imbalance and would lead to a disease.

Acupuncture or needle therapy for treating various ailments have been known for at least four thousand years. Different materials, including stone, wood and, in recent years, metal were used for manufacturing acupuncture needles. Twentieth century discoveries in biomedicine gave better understanding about transmission of the infectious diseases. Based on this knowledge, new much stricter requirements for safety and sterility during acupuncture procedure were imposed. Modern day acupuncturists in the USA and other developed countries use sterile, disposable needles made of stainless steel or, sometimes, other metals. In 1996, FDA has approved acupuncture needles as medical equipment, acknowledging safety and effectiveness of the procedure. Many hospitals have started incorporating acupuncture as part of their services over last years.

On the other hand, the healing effect of water therapy is known since ancient times, and at the present time water therapy finds ever growing application for treating various diseases, as well as for physical exercises, rehabilitation of athletes and patients after surgical operations, traumas, etc. Treatment in water may be carried out even without physical exercises or movements, but rather solely due to variation of water temperature. Such treatment is based on specific physiological responses water produces in patients. These physiological responses are the following: hydrostatic pressure evens out tactile input, helps reduce tactile defensiveness due to generalized constant sensory input which helps "turn off" the rectile system; warm water promotes inhibition of spastic muscles, promotes relaxation and decreases pain, increases superficial and peripheral circulation, intensifies blood supply to muscles, decreases joint compression force, prepares connective tissue for stretching, increases body temperature, and produces many other useful effects.

For the acupuncture prospective, various types of temperature modifying tools have been used in acupuncture for centuries. They were used to enhance the therapeutic effect of the acupuncture treatment. External application of heat and heat generating herbs were utilized to produce a physiological response to that obtained during treatment with warm water. A special herb, Artemisia Vulgaris, which is burnt on or over the skin, infrared heaters, herbal compresses with warming properties are among popular acupuncturist tools for altering temperature. At the same time, if a patient is placed in a tub in which temperature can be controlled, a guaranteed systemic response in the patient is assured, and the bodily processes can be shifted in a desired direction. A good example from the clinical practice is the acupuncture treatment of the muscular and skeletal problems. The muscular and skeletal conditions, with damage limited primarily to soft tissues, respond extremely well to a combination of acupuncture with heat. Both methods enhance the blood circulation, relax muscles and tendons, increase the metabolic rate, and promote healing. Low back pains, sprains, strains, repetitive motion disorders, and many others fall into this category.

It was, however, impossible to utilize acupuncture under water because of hygienic problems, problems of sterility and, therefore, a risk of infection through the use of conventional acupuncture techniques.

OBJECTS OF THE INVENTION

It is an object of the present invention to provide a method for acupuncture without a risk of infection and without problems associated with sterility of needles. Another object is to provide a method for acupuncture which combines the use of acupuncture with variation in the body temperature in warm water and with external application of useful herb. Still another object is to provide a hydrotherapeutic acupuncture which produces a synergistic healing effect, which is stronger than a mere sum of effects of acupuncture and water therapy. Another object of the invention is to provide a device for acupuncture that can be conducted under water under sterile conditions with the use of disposable needles without a contact of the acupuncture points with water.

SUMMARY OF THE INVENTION

Figure 1:
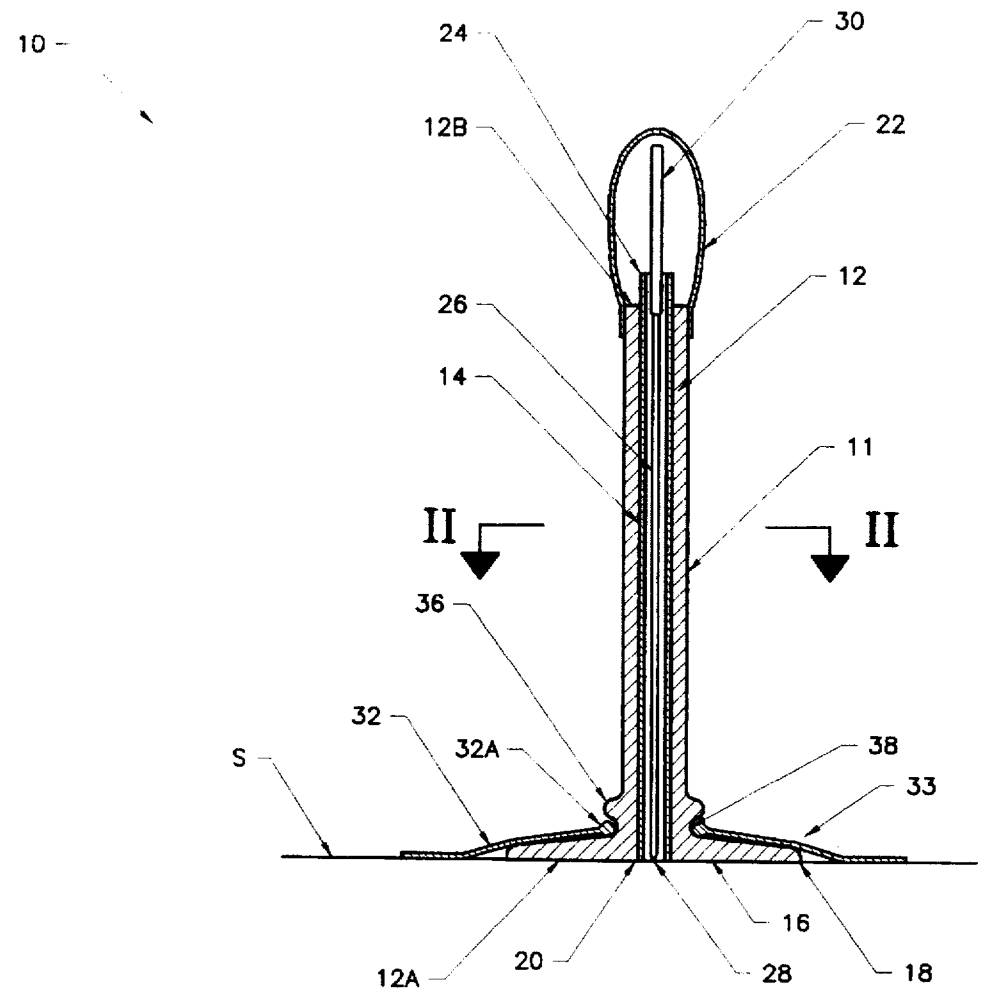
FIG. 1 is a vertical sectional view of the device for acupuncture.

An acupuncture method developed by the inventors consists of three steps: 1) applying an acupuncture device to a patient's body; 2) conducting the acupuncture treatment with the patient immersed in water; 3) removing the acupuncture device from the patient's body when the patient is out of the water. The device for carrying out the method is in the form of a sterile acupuncture needle, which is placed into an enclosure having a sealing needle control member at one end and a flexible sealing support at the other end. The device is attached to the patient's body and is sealed in place by a water-proof tape.

DETAILED DESCRIPTION OF THE INVENTION

The authors, who have many years of experience—one in the field of water therapy and another in the field of acupuncture, have unexpectedly found that acupuncture treatment in water results in a synergistic effect which is stronger than a mere sum of effects of acupuncture and water therapy performed separately. In order to solve problems of sterility for conducting their tests of hydrotherapeutic acupuncture the authors have invented a special device for underwater acupuncture.

Prior to the description of the method of treatment, it would be expedient to describe a device for carrying out the method. This device is shown in the attached drawings, wherein FIG. 1 is a vertical sectional view of the device for underwater acupuncture and FIG. 2 is a sectional view of the device of FIG. 1, taken along line II—II.

A device for acupuncture generally shown at 10 has an enclosure 11. Enclosure 11 consists of a tube 12 having a first end 12*a* and a second end 12*b*, a through axial passage 14, and a base 16 at first end 12*a* of tube 12. The base has a periphery 18 and an inside area 20. Enclosure 11 also has a needle control member 22. The needle control member is installed on second end 12*b* of tube 12 and seals off this end of the tube. It is preferred that needle control member 22 be made of an elastic material such as rubber, plastic and the like, which is capable of performing the sealing function and allowing a needle to be controlled from outside. It is also preferred that needle control member 22 narrow from second end 12*b* of tube 12 toward the distal end as shown in FIG. 1. This facilitates manipulation. Tube 12 can be made of a light metal alloy, plastic and similar materials. It is, however, preferred that tube 12 be made of a transparent plastic for the purpose to be explained below. A tubular guide 24 is inserted in tube 12 through its open end 12*a*. The length of this tubular guide is greater than the length of tube 12. This is necessary to facilitate removal of the tubular guide from the tube by pushing it off. The inside diameter of tubular guide 24 is greater than the diameter of an acupuncture needle to be used with the device. The outside diameter of tubular guide 24 is only slightly smaller than the inside diameter of the passage 14 for the purpose to be explained below. Tubular guide 24 can be made of any plastic material or glass, and it is preferred that it be made of a transparent material. An acupuncture needle 26 has a tip 28 and a handle 30. The acupuncture needle is inserted into enclosure 11 through its end 12*a*, handle 30 first, and extends in tubular guide 24, the handle 30 protruding outside the tubular guide into the interior of needle control member 22. With this construction, handle 30 of the acupuncture needle can be grasped through needle control member 22 to be guided, pushed in, and pulled out. The conical shape of needle control member 22 facilitates these manipulations.

Figure 2:
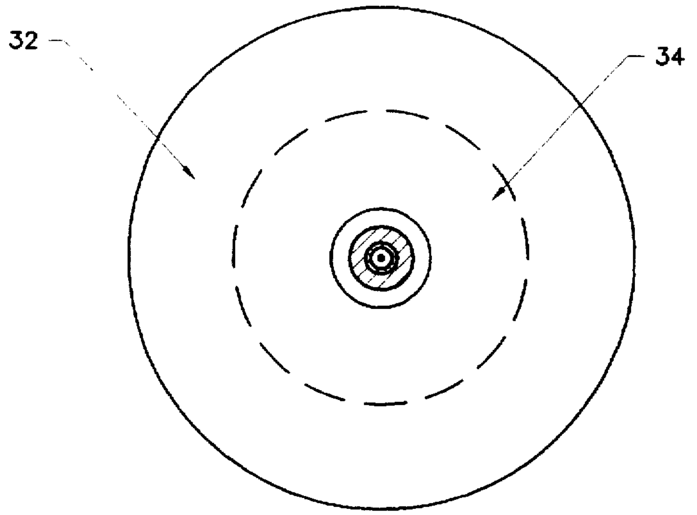
FIG. 2 is a sectional view of the device of FIG. 1, taken along line II—II.

As shown in FIGS. 1, 2, the device has an adhesive tape member 32 applied to base 16 of enclosure 11. This adhesive tape member can be configured in any appropriate manner to fit to a part of a patient's body in which an acupuncture point to be treated is located. In the illustrated embodiment, the adhesive tape member is of a circular configuration. In any case, the adhesive tape member is applied to base 16 to extend outside its periphery 18 for the purpose to be described below. It is preferred that adhesive tape member 32 have a non-sticky area 34 (FIG. 2), which corresponds to a zone between periphery 18 and inside area 20 of the base. It is important that non-sticky area 34 be smaller than the base area, so as to have the adhesive contact between adhesive tape member 32 and base 16. Non-sticky area 34 can be formed during manufacture of adhesive tape member 32 or by application of a piece of a non-sticky material to a respective area of adhesive tape member 32.

It will be apparent from the above description that base 16 and adhesive tape member 32 form a sealing and mounting flange 33 for affixing acupuncture device 10 to the patient's skin. This flange 33 is designed for holding the device to the skin and for sealing open end 12*a* of tube 12.

To seal off the area of contact between adhesive tape member 32 and enclosure 11, tube 12 has a collar 36 adjacent to base 16. Collar 36 and base 16 define a groove 38, and an inner edge 32*a* of adhesive tape member 32 is received in this groove. Inner edge 32*a* of adhesive tape 32 is made in the form of a solid elastic ring. It is preferable to make adhesive tape member 32 of any elastic material, preferably, of rubber. Inner edge 32*a* is designed for inserting into groove 38 to assure sealing. The inside diameter of the ring that defines inner edge 32*a* is smaller than the outside diameter of tube 12 in groove 38.

The above-described device is assembled in the following manner. Enclosure 11 (especially its base 16 and passage 14) is cleaned and sterilized. The acupuncturist holds enclosure 11 at tube 12 with needle control member 22 facing down and inserts tubular guide 24 into passage 14 through open end 12*a* of tube 12. Tubular guide 24 is sterile and disposable. Acupuncture needle 26 is a disposable sterile needle in compliance with the FDA requirements. The acupuncture needle is dropped into tubular guide 24, handle 30 first. Having assembled the device as described above, the acupuncturist applies base 16 of enclosure 11 to the skin of a patient to be treated in such a manner that the outer end of tubular guide 24 covers the area around the acupuncture point for treatment. The acupuncturist then applies sterile adhesive tape member 32 to base 16 and skin S of the patient to affix the device to the patient. Inner edge 32*a* of adhesive tape 32 is then put on tube 12 and pushed along the tube until it snaps into groove 38 defined by collar 36 and base 16 to seal the zone of contact of the inner edge of the adhesive tape with enclosure 11. In this position, the device is attached to the patient's body, acupuncture needle 26 is positioned in the zone of the acupuncture point to be treated, needle handle 30 protrudes from tubular guide 24 in the interior of needle control member 22, and the interior of the device, including the acupuncture point, is sealed off by means of needle control member 22 and adhesive tape member 32. As the outside diameter of tubular guide 24 is only slightly smaller than the diameter of passage 14, the tubular guide is held by friction within tube 12, thus facilitating manipulation of the acupuncture needle.

In accordance with the invention a method for acupuncture comprises the following steps: putting an acupuncture needle, having a tip and a handle, into an enclosure open on one end and sealingly closed on opposite end, the tip being on the side of the open end of said enclosure; bringing the aforementioned one end of the enclosure in contact with the skin of a patient to define an area of contact of the aforementioned open end of the enclosure with the skin so that the tip of the needle facing the skin; sealing the contact area; and conducting a hydrotherapeutic acupuncture procedure.

In accordance with one embodiment of the method, the hydrotherapeutic acupuncture procedure may be carried out by first placing the patient into the vessel, connecting the hydrotherapeutic acupuncture device to the skin of the patient, sealing the zone of contact of the device with the skin, and then filling the vessel with water and conducting the hydrotherapeutic treatment in combination with acupuncture. Water may be then drained, the patient is removed from the vessel, and the enclosure with needles is disconnected.

In accordance with another embodiment of the method, the patient with preliminary installed and sealed hydroacupuncture devices may be immersed into the vessel which has been filled with water, and then the hydrotherapeutic treatment combined with acupuncture is conducted as described above.

More specifically, in the last-mentioned case, the patient is placed into a temperature-controlled vessel (not shown) filled with liquid, e.g., with water. The patient is immersed in water to such an extent that the parts of the body, which have to be treated be located under water, so as to be exposed to the desired temperature conditions. It is understood that some of the acupuncture needles will be thus immersed in water. As these needles are sealed off by means of the acupuncture device according to the invention, the acupuncture points, which have to be penetrated by the needles, will not be in contact with water to avoid any infection.

It is preferred that the acupuncture needles be pushed into the skin of the patient when he/she is immersed in the water, because it would not be desirable in many applications that the patient move with the needles inserted. The acupuncturist grasps needle handle 30 through needle control member 22, points the needle to the acupuncture point, and pushes the needle through the skin. When the acupuncturist pushes control member 22 down, the pressure of air entrapped in a closed and sealed enclosure 11 is increased. This increased air pressure is compensated for by the presence of non-sticky portion 34 located over base 16. The fact that the tube and tubular member are made of a transparent material facilitates insertion of the acupuncture needle at the exact point of treatment.

After insertion of the acupuncture needle (needles), a water treatment session is carried out following a desired procedure, with the difference from the conventional water treatment that the patient also has acupuncture needles inserted at the acupuncture points. Other treatment remedies, such as herb, medication, etc., can be used in combination with this treatment as prescribed by the physician. The patient may be asked to do certain exercises. During the treatment, a pressure gradient exists between the interior of enclosure 11 and water. This creates a cup suction effect providing an additional stimulation at the point being treated. The procedure takes a predetermined time, e.g., for 15 to 45 minutes depending on the patient condition, and water temperature can be varied during the treatment session to achieve the desired therapeutic effect.

When the treatment session is over, the acupuncturist lifts off acupuncture needle 26 by pulling handle 30 up through needle control member 22, without completely withdrawing the needle from the skin. This is necessary to ease the patient's movement when the patient leaves the vessel. It is preferred that the needle be not withdrawn completely to avoid eventual bleeding that may contaminate tube 12 and its base 16. The patient is asked or helped to leave the vessel. When the patient is out of water, adhesive tape member 32 is removed, and the acupuncturist removes device 10 from the skin by grasping at tube 12 while holding handle 30 of acupuncture needle 26 through needle control member 22. This results in needle tip 28 being withdrawn from the skin. Any blood that can eventually be on the needle can contaminate tubular guide 24 that is disposable. The acupuncturist then releases handle 30 of acupuncture needle 22 that can be disposed into an appropriate container (not shown) and pushes tubular guide 24 out of tube 12 by acting through needle control member 22 upon the end of the tubular guide, which projects into the interior of the needle control member, because the tubular guide is longer than tube 12. The tubular guide is thus also disposed. The acupuncture point on the patient's skin is treated with an antiseptic. Enclosure 11, including tube 12 and needle control member 22 is cleaned and sterilized for reuse, and adhesive tape 32 is disposed. It is understood that if there is any blood on tube 12 and/or its base 16, e.g., as a result of the acupuncture needle being completely withdrawn before removal of the acupuncture device from the skin, tube 12 has to be disposed as well.

Various modifications and alterations can be made, without going beyond the spirit and scope of the appended claims. Thus, mounting and sealing flange 33 can be in the form of a suction cup that can be with or without an adhesive tape to guarantee stability of the device. Sealing of the point between the adhesive tape member and the tube can be assured by a collet device. The effect of the acupuncture will be enhanced even though a part of the body with the needles is not immersed in water, provided a part of the body is still immersed in water. The elastic ring may be made as a separate part that is sealingly placed over the inner edge of the adhesive tape. The adhesive tape member may be square in shape rather than circular.

We claim:

1. A method for hydrotherapeutic acupuncture comprising the steps of:

putting at least one acupuncture needle, having a tip and a handle, into at least one enclosure open on one end and sealingly closed on an opposite end, said tip being on the side of said open end of said enclosure;

placing said patient into a hydrotherapy vessel;

bringing said one end of said at least one enclosure in contact with the skin of a patient to define an area of contact of said one end of said enclosure with the skin, with said tip facing an acupuncture point of the skin;

sealing said contact area;

filling said vessel with a liquid under temperature-controlled conditions;

causing said tip of said at least one acupuncture needle to penetrate the skin to start an acupuncture treatment session;

controlling the temperature of the liquid while maintaining said tip in the skin of said patient for a predetermined period of time;

withdrawing said tip of said at least one needle from the skin of the patient after expiration of said predetermined period of time, while maintaining said contact area under sealed conditions;

having the patient leave said vessel; and unsealing said contact area and disconnecting said at least one enclosure with said at least one needle from the skin of said patient.

2. The method of claim 1, wherein, after hydrotherapeutic acupuncture procedure is over and prior to said step of having the patient leave said vessel, said liquid is drained from said vessel.

3. The method of claim 1, wherein said enclosure comprises a tube, having at said open end a sealing and holding flange engageable with the patient's skin and a through axial passage, a needle control means, which is installed on, and seals off, said opposite end, and a tubular guide member removably inserted into said through axial passage of said tube, said tubular guide being longer than said tube.

4. The method of claim 3, wherein said tube has, at said open end, a base which has a periphery and an inside area, said sealing and mounting flange being formed by said base and by an adhesive tape member, which extends outside said base.

5. The method of claim 4, wherein said adhesive tape member has a non-sticky area in the zone between said periphery and said inside area of said base.

6. The method of claim 4, wherein a sealing means is provided between said tube and said adhesive tape member.

7. The method of claim 6, wherein a sealing means is provided between said tube and said adhesive tape.

8. The method of claim 7, wherein said adhesive tape has an inner edge, said sealing means comprising an elastic ring member made integrally with said inner edge and a collar on said tube adjacent to said base, said collar defining a groove with said base, said groove having a diameter and receiving said elastic ring, said diameter of said elastic ring being smaller than said diameter of said groove.

9. The method of claim 6, wherein said adhesive tape has an inner edge, said sealing means comprising an elastic ring member made integrally with said inner edge and a collar on said tube adjacent to said base, said collar defining a groove with said base, said groove having a diameter and receiving said elastic ring, said diameter of said elastic ring being smaller than said diameter of said groove.

10. The method of claim 1, wherein said enclosure comprises a tube, having at said open end a sealing and holding flange engageable with the patient's skin and a through axial passage, a needle control means, which is installed on, and seals off, said opposite end, and a tubular guide member removably inserted into said through axial passage of said tube, said tubular guide being longer than said tube.

11. The method of claim 10, wherein said tube has, at said open end, a base which has a periphery and an inside area, said sealing and mounting flange being formed by said base and by an adhesive tape member, which extends outside said base.

12. The method of claim 11, wherein said adhesive tape member has a non-sticky area in the zone between said periphery and said inside area of said base.

13. The method of claim 12, wherein a sealing means is provided between said tube and said adhesive tape member.

14. The method of claim 13, wherein said adhesive tape has an inner edge, said sealing means comprising an elastic ring member made integrally with said inner edge and a collar on said tube adjacent to said base, said collar defining a groove with said base, said groove having a diameter and receiving said elastic ring, said diameter of said elastic ring being smaller than said diameter of said groove.

15. The method of claim 13, wherein said adhesive tape has an inner edge, said sealing means comprising an elastic ring member made integrally with said inner edge and a collar on said tube adjacent to said base, said collar defining a groove with said base, said groove having a diameter and receiving said elastic ring, said diameter of said elastic ring being smaller than said diameter of said groove.

16. The method of claim 12, wherein a sealing means is provided between said tube and said adhesive tape.

17. A method for hydrotherapeutic acupuncture comprising the steps of:

putting at least one acupuncture needle, having a tip and a handle, into at least one enclosure open on one end and sealingly closed on an opposite end, said tip being on the side of said open end of said enclosure;

bringing said one end of said at least one enclosure in contact with the skin of a patient to define an area of contact of said one end of said enclosure with the skin, with said tip facing an acupuncture point of the skin:

sealing said contact area:

filling a hydrotherapy vessel with a liquid under temperature-controlled conditions;

placing said patient into said vessel filled with said liquid;

causing said tip of said at least one acupuncture needle to penetrate the skin to start an acupuncture treatment session;

controlling the temperature of said liquid while maintaining said tip in the skin of said patient for a predetermined period of time;

withdrawing said tip of said at least one needle from the skin of said patient after expiration of said predetermined period of time, while maintaining said contact area under sealed conditions;

having the patient leave said vessel; and unsealing said contact area and disconnecting said at least one enclosure with said at least one needle from the skin of said patient.

18. The method of claim 17, wherein, after hydrotherapeutic acupuncture procedure is over and prior to said step of having the patient leave said vessel, said liquid is drained from said vessel.

19. The method of claim 17, wherein said enclosure comprises a tube, having at said open end a sealing and holding flange engageable with the patient's skin and a through axial passage, a needle control means, which is installed on, and seals off, said opposite end, and a tubular guide member removably inserted into said through axial passage of said tube, said tubular guide being longer than said tube.

20. The method of claim 19, wherein said tube has, at said open end, a base which has a periphery and an inside area, said sealing and mounting flange being formed by said base and by an adhesive tape member, which extends outside said base.

21. The method of claim 20, wherein said adhesive tape member has a non-sticky area in the zone between said periphery and said inside area of said base.

22. The method of claim 20, wherein a sealing means is provided between said tube and said adhesive tape member.

23. The method of claim 22, wherein a sealing means is provided between said tube and said adhesive tape.

24. The method of claim 23, wherein said adhesive tape has an inner edge, said sealing means comprising an elastic ring member made integrally with said inner edge and a collar on said tube adjacent to said base, said collar defining a groove with said base, said groove having a diameter and receiving said inner edge of said adhesive tape and said elastic ring, said diameter of said elastic ring being smaller than said diameter of said groove.

25. The method of claim 22, wherein said adhesive tape has an inner edge, said sealing means comprising an elastic ring member made integrally with said inner edge and a collar on said tube adjacent to said base, said collar defining a groove with said base, said groove having a diameter and receiving said inner edge of said adhesive tape and said elastic ring, said diameter of said elastic ring being smaller than said diameter of said groove.

26. A device for acupuncture, comprising an acupuncture needle having a tip and a handle, said device further comprising:

an enclosure comprising a tube defining an axial passage and having a first end and a second end, a sealing and holding flange engageable with a patient's skin, and a needle control member installed on, and sealing off, said second end of said tube;

a tubular needle guide having an inside diameter and an outside diameter, said tubular needle guide being insertable into said axial passage of said tube, said tubular needle guide being longer than said tube, the inside diameter of said tubular guide being greater than the diameter of said acupuncture needle.

27. The device of claim 26, wherein said tube has a diameter and a base at said first end, said base having a periphery and an inside area, and said sealing and holding flange comprising said base and an adhesive tape member applied to said base, said adhesive tape member extending outside said periphery of said base.

28. The device of claim 27, wherein said needle control member is made of an elastic material.

29. The device of claim 27, wherein said adhesive tape member has a non-sticky area in the zone between said periphery and said inside area of said base, said device further comprising a sealing means between said adhesive tape member and said enclosure.

30. The device of claim 29, wherein said sealing means comprises an elastic ring and a collar on said tube adjacent to said base, said collar and said base forming a groove which has a diameter, said groove receiving said elastic ring, said elastic ring having an inside diameter, said inside diameter of said elastic ring being smaller than said diameter of said tube in said groove.

31. The device of claim 26, wherein said needle control member is made of an elastic material.

32. The device of claim 31, wherein said adhesive tape member has an inner edge and a non-sticky area in the zone between said periphery and said inside area of said base, said device further comprising a sealing means between said adhesive tape member and said enclosure, said sealing means comprises an elastic ring made integrally with said inner edge and a collar on said tube adjacent to said base, said collar and said base defining a groove which receives elastic ring, said elastic ring having an inside diameter, said inside diameter of said elastic ring being smaller than said diameter of said tube in said groove.

33. A device for acupuncture, comprising an acupuncture needle having a tip and a handle, said device further comprising:

an enclosure comprising a tube having a diameter, a first end and a second end and defining an axial passage;

a needle control member made of an elastic material installed on, and sealing off, said second end of said tube, a base at said first end, said base having a periphery and an inside area, and an adhesive tape member applied to said base, said adhesive tape member having an inner edge and extending outside said periphery of said base and having a non-sticky area in the zone between said periphery and said inside area of said base;

a tubular needle guide having an inside diameter and an outside diameter, said tubular needle guide being insertable into said axial passage of said tube, said tubular needle guide being longer than said tube, the inside diameter of said tubular guide being greater than the diameter of said acupuncture needle;

a sealing means between said adhesive tape member and said enclosure, said sealing means comprising an elastic ring made integrally with said inner edge and collar on said tube adjacent to said base, said collar defining with said base a groove, said groove receiving said elastic ring in said groove, said elastic ring having an inside diameter, said inside diameter of said elastic ring being smaller than said diameter of said tube in said groove.

* * * * *